United States Patent [19]
Davis et al.

[11] Patent Number: 5,928,669
[45] Date of Patent: Jul. 27, 1999

[54] LYMPHATIC DELIVERY METHODS

[75] Inventors: Stanley S. Davis; Lisbeth Illum; Nicola Christy; Moein Moghimi, all of Nottingham, United Kingdom

[73] Assignee: Danbiosyst UK Limited, Nottingham, United Kingdom

[21] Appl. No.: 09/094,959

[22] Filed: Jun. 15, 1998

Related U.S. Application Data

[62] Division of application No. 08/374,671, filed as application No. PCT/GB93/01596, Jul. 28, 1993, Pat. No. 5,792,475.

[30] Foreign Application Priority Data

Jul. 28, 1992 [GB] United Kingdom .................. 9216082

[51] Int. Cl.[6] ...................................... A61K 9/51
[52] U.S. Cl. .......................... 424/489; 424/490
[58] Field of Search .................... 424/489, 490; 428/402, 403

[56] References Cited

U.S. PATENT DOCUMENTS

| | | |
|---|---|---|
| 4,904,479 | 2/1990 | Illum . |
| 5,462,750 | 10/1995 | Kossovsky et al. . |
| 5,470,583 | 11/1995 | Na et al. . |
| 5,543,158 | 8/1996 | Gref et al. . |
| 5,560,931 | 10/1996 | Eickhoff et al. ........................ 424/489 |
| 5,565,215 | 10/1996 | Gref et al. . |
| 5,571,536 | 11/1996 | Eickhoff et al. ........................ 424/489 |

FOREIGN PATENT DOCUMENTS

| | | |
|---|---|---|
| 2 108 967 | 5/1983 | United Kingdom . |
| WO 94/02068 A1 | 2/1994 | WIPO . |
| WO 94/08624 A2 | 4/1994 | WIPO . |
| WO 94/21240 A2 | 9/1994 | WIPO . |

OTHER PUBLICATIONS

Allen, et al., "Subcutaneous Administration Of Liposomes: A Comparison With The Intravenous And Intraperitoneal Routes Of Injection," *Biochim. Biophys. Acta* 1150:9–16 (1993).

Bergqvist, et al., "Particle Sizing and Biokinetics Of Interstitial Lymphoscintigraphic Agents," *Nuclear Med.* 13(1):9–19 (1983).

Bergqvist, et al., "The Characterization Of Radiocolloids Used For Administration To The Lymphatic System" in *Microspheres And Drug Therapy, Pharmaceutical, Immunological And Medical Aspects* (Davis et al., eds.) p. 263 (Elsevier Science Publishers 1984).

Brindley, et al., "The Surface Characterization of Model Charged and Sterically Stabilized Polymer Colloids by SSIMS and X.p.s.," *Polymer* 33(5):1112–15 (1992).

Carstensen, et al., "Adsorption of Ethoxylated Surfactants on Nanoparticles. I. Characterization by Hydrophobic Interaction Chromatography," *Int'l J. Pharmaceutics* 67(1):29–37 (1991).

Christy, et al., "Effect Of Size On The Lymphatic Uptake Of A Model Colloid System," Proceed. Intern. Symp. Control. Rel. Bioact. Mater. 19 (1992).

(List continued on next page.)

*Primary Examiner*—Robert Harrison
*Attorney, Agent, or Firm*—Arnall Golden & Gregory, LLP

[57] ABSTRACT

A composition for delivering an active agent to the lymphatic system comprises a plurality of colloidal particles and an active agent associated with each particle, wherein the surface of each particle has a hudrophobicity ratio as defined of less than 10, or wherein a modifying agent is adsorbed onto the surface of each particle such that the modifying agent gives an advancing contact angle as defined of less than 60° or wherein the adsorbed layer thickness as defined is less than 10 nm or the albumin uptake ratio is between 0.2 and 0.5. The composition may satisfy one or more of these requirements. Preferred modifying agents are non-ionic surfactants, in particular block copolymers containing polyethyleneglycol.

17 Claims, 3 Drawing Sheets

OTHER PUBLICATIONS

Cosgrove, et al., "An Experimental Study Of Polymer Conformations At The Solid/Solution Interface" In *Adsorption From Solution* (Ottewill et al., eds.) pp. 287–296 (Academic Press 1983).

Costello, et al., "Investigations Of The Properties Of Aqueous Sterically Stabilized Dispersions," *J. Colloid Interface Sci.* 152(1):237–46 (1992).

Harris, et al., "Determination Of The Adsorption Of Surface Active Agents On Latex Particles By Small Angle Scattering" in *Adsorption From Solution* (Ottewill et al., eds.) pp. 139–154 (Academic Press 1983).

Huh, et al., "A Radiation–Induced Bonding Of Iodine At The Surface Of Uniform Polystyrene Particles," *Radiation Res.* 60:42–53 (1974).

Kaledin, et al., "Subcutaneously Injected Radiolabeled Liposomes: Transport To The Lymph Nodes In Mice," *J. Nat. Cancer Inst.,* 69(1):67–71 (1982).

Kayes, et al., "Adsorption Characteristics Of Certain Polyoxyethylene–Polyoxpropylene Block Co–Polymers On Polystyrene Latex," *Colloid & Polymer Sci.* 257:622–29 (1979).

Kim, et al., "Lymph Node Targeting and Pharmacokinetics Of [$^3$H]methotrexate–encapsulated Neutral Large Unilamellar Vesicles And Immunoliposomes," *Int'l J. Pharmaceutics* 98:9–18 (1993).

Klibanov, et al., "Amphiphatic Polyethyleneglycols Effectively Prolong The Circulation Time of Liposomes," *FEBS* 268(1):235–37 (1990).

Litzinger, et al., "Amphiphatic Poly(ethylene glycol) 5000–Stabilized Dioleoylphosphatidylethanolamine Liposomes Accumulate In Spleen," *Biochim. Biophys. Acta* 1127:249–54 (1992).

Mangat, et al., "Lymph Node Localization Of Non–Specific Antibody–Coated Liposomes," *Life Science* 36:1917–25 (1985).

MAAS, et al., "Ultrasmall Magnetite Particles Coated With Polyethyleneglycol As Contrast Agent In MRI Of Experimental Abscesses: An Animal Study In Mini–Pigs" in *Abstracts 10th Meeting: Society Of Magnetic Resonance In Medicine,* vol. 2 (1991).

Müller, et al., "Surface Characterization Of Colloidal Drug Carriers For Drug Targeting By Aqueous Two–Phase Partitioning" in *Separations Using Aqueous Phase Systems: Application In Cell Biology And Biotechnology* (Fisher et al., eds.) pp. 149–155 (Plenum Press, New York 1987).

Müller, et al., "Particle Charge And Surface Hydrophobicity Of Colloidal Drug Carriers" in *Targeting Of Drugs With Synthetic Systems* (Gregoriadis et al., eds.) pp. 239–263 (Plenum Press, New York 1986).

Osborne, et al., "Radionuclide–Labelled Liposomes—A New Lymph Node Imaging Agent," *Int'l J. Nucl. Med. Bio.* 6:75–83 (1979).

Ottewill, et al., "Non–Ionic Polystyrene Latices In Aqueous Media," *British Polymer J.* 19(5):435–40 (1987).

Patel, "Fate Of Liposomes In The Lmphatics" in *Liposomes As Drug Carriers* (Gregoriadis, ed.) Ch. 4, pp. 51–62 (John Wiley & Sons Ltd. 1988).

Troster, et al., "Contact Angles Of Surfactants With A Potential To Alter Body Distribution Of Colloidal Drug Carriers On Poly(methyl methacrylate) Surfaces," *Int. J. Pharm.* 45:91–100 (1988).

Tümer, et al., "Fate Of Cholesterol–Rich Liposomes After Subcataneous Injection Into Rats," *Biochim. Biophy. Acta.* 760:119–25 (1983).

LYMPHATIC DELIVERY METHODS

RELATED APPLICATIONS

This is a division of U.S. Ser. No. 08/374,671, filed Apr. 14, 1995, U.S. Pat. No. 5,792,475, which is the national phase of PCT/GB93/01596, filed Jul. 28, 1993, and British application GB 9216082.9, filed Jul. 28, 1992.

The present invention relates to a lymphatic delivery composition, and more particularly to a composition for delivering an active agent to the lymphatic system.

The lymphatic system has an important role in transporting body fluids and particulate materials to include proteins, fat particles, etc. Large proteins and certain cells (lymphocytes) pass from the blood plasma into the tissue fluid and it is the major function of the lymph to return these essential components to the blood circulation. The lymph also plays an important role in transporting the products of fat digestion in the gastrointestinal tract, the chylomicrons, into the blood circulation. The properties of the lymphatic system have been reviewed in detail by J. M. Yoffrey and F. C. Courtice (Lymphatics, lymph and the lymphomyeloid complex, Academic Press, London, 1970). The lymphatic system also plays an important role in the spread of tumours. Malignant cells can enter the lymphatic system and become captured by lymph nodes where secondary tumours can be produced. Eventually the whole of the lymph chain can be involved. The lymph can also be involved in the spread of tumours to other organs, for example the lungs. Consequently there is considerable need for a method of examining the lymphatic drainage and lymph nodes in the diagnosis and treatment of malignant diseases. This subject has been reviewed extensively by S. E. Strand and others (L. Bergquist et al. in Microspheres and Drug Therapy, Immunological and Medical Aspects p.263 (Edited by Davis et al.) Elsevier 1984).

It is well known that colloidal particles can have an important role in characterising the properties of the lymphatic system as well as a possible role in delivering drugs to the lymphatic system. The use of colloidal particles as radiodiagnostic agents has been reviewed by Strand et al. (Bergquist et al. Seminars in Nuclear Med. 12 (1983) 9–19). A wide range of materials has been examined to include solid particles, emulsions and vesicles (liposomes). The distribution of colloidal agents depends strongly on their particle and colloids suggested for lymphoscintigraphy were found to have a median size of about 40–60 nm. Uptake into regional lymph nodes after, for example, subcutaneous administration is quite small and values from 1–10% are typical after 2–5 hours (Strand, S. E. CRC Crit. Rev. Drug Carrier Systems 6 (1989) 211–237).

A targeting system for the delivery of diagnostic and therapeutic agents to the lymphatic system should have the following characteristics:

(i) spread well from the injection site and
(ii) provide good uptake in both primary and secondary regional lymph nodes.

Various attempts have been made to increase lymphatic uptake by change in particle size and particle number and particle nature and these have been reviewed by Strand (CRC Crit. Rev. Drug Carrier Systems 6 (1989) 211–237). With liposome systems the best recorded level of uptake in the lymph nodes is from 1–2% at 48 hours. This can be increased to about 5% by the attachment of antibodies. (Patel, H. M. In Liposomes as drug carriers, Ed. G. Gregoriadis, p. 51 John Wiley, 1988, Kaledin, J. et al. Nat. Cancer Inst. 69 (1982) 67–71, Tuner, A. et al. Biocim. Biophy. Acta 760 (1983) 119–125).

GB 2108967 describes the admixture of colloidal albumin particles with poloxamers and ethoxylated surfactants of the Cremophor series and measurements on lymphatic uptake are described. The quantities sequestered in lymph nodes arm reported for times of 2 hours after administration. For the poloxamer materials only the hydrophilic materials containing 80% ethylene oxide content were examined. The uptake in the primary lymph nodes was increased with values as high as 17% reported for Poloxamer 238. For Poloxamer 188 about 13% of the colloid was captured in the primary nodes. However, only 1% was reported to be found in the secondary nodes.

High uptake into both primary and secondary lymph nodes has not been achieved and this, is a big disadvantage for delivery of diagnostic and therapeutic agents to the lymphatic system.

Illum and others have described the use of surfactants and in particular the poloxamers and poloxamines for drug delivery and drug targeting applications in the systemic circulation. In U.S. Pat. No. 4,904,479 Illum describes how the materials poloxamer 407 and poloxamine 908 can be used to target colloidal carriers to the bone marrow of the rabbit or retain such particles in the systemic circulation. These prior art materials have been studied in the work leading to the present invention; neither material has been found to have advantage in targeting colloidal particles to the regional lymph nodes.

We have now found, very surprisingly, that it is possible to greatly increase the uptake of colloidal particles in regional lymph nodes by modifying the hydrophobicity/hydrophilicity of the surface of small colloidal particles. In this way we have been able to deliver more than 20% of the administered dose into the regional lymphnodes of the rat at 24 hours following s.c. injection. Moreover, the uptake in the secondary lymph nodes has been increased greatly. We have found that the type of surface modification adopted is important in determining lymph node uptake. If the particles are too hydrophobic they are retained at the site of injection. If the particles are too hydrophilic they are transported from the site of injection through the lymph nodes and into the circulation. Thus, we have found that coatings with intermediate hydrophilic/hydrophobic properties are to be preferred. Such systems are well transported from the site of injection and are well retained in the lymph nodes (primary and secondary) by a process of capture by the resident macrophages. This process of uptake may involve a receptor mediated step where particles are coated with certain lymph proteins known as opsonins.

Thus, one aspect of the present invention provides a composition for delivering an active agent to the lymphatic system comprising a plurality of colloidal particles and an active agent associated with each particle, wherein the surface of each particle is modified to give a hydrophobicity ratio as herein defined of less than 10 and preferably less than 5. The hydrophobicity ratio is measured by the method of hydrophobic interaction chromatography using butyl agarose.

In a further aspect the invention provides a composition for delivering an active agent to the lymphatic system comprising a plurality of colloidal particles and an active agent associated with each particle, a modifying agent being adsorbed onto or attached to the surface of each particle, wherein the modifying agent gives an advancing contact angle as herein defined of less than 60°.

The advancing contact angle is that obtained when the modifying agent is adsorbed or attached to the surface of polystyrene at a concentration providing a plateau in the adsorption isotherm.

In a still further aspect, the invention provides a composition for delivering an active agent to the lymphatic system comprising a plurality of colloidal particles and an active agent associated with each particle wherein a modifying agent is adsorbed or attached onto the surface of each particle such that the thickness of the layer of modifying agent is less than 10 nm and preferably the layer thickness is 0.8 to 4.0 nm. The layer thickness is by photon correlation spectroscopy using uncoated particles as control, or by rheological measurements.

A still further aspect of the invention provides a composition for delivering an active agent to the lymphatic system comprising a plurality of colloidal particles and an active agent associated with each particle wherein a modifying agent is adsorbed onto or attached to the surface of each particle such that the albumin uptake ratio (AUR) of the surface as herein defined is between 0.2 and 0.5. The albumin uptake ratio is defined as the ratio of the amount of human serum albumin adsorbed to test particles to the amount adsorbed to control polystyrene particles.

The above requirements may be used as alternative measurements of the surface properties of particles of the composition according to the invention or may be used in combination such that the composition satisfies more than one of the requirements.

The term active agent as used herein is defined as a pharmaceutically or therapeutically active agent or a diagnostic agent.

The active agent may be associated with the particles by any well known technique, but should be in such a way that the active agent remains associated with the particles until the point of uptake of the particles by the lymph nodes.

Preferably, the surface of each particle is modified by adsorption or attachment of a modifying agent. The term "modifying agent" is used herein to describe any agent which modifies the surface hydrophobicity/hydrophilicity of the particle. Preferred materials are non-ionic surfactants, and particularly preferred materials are members of the poloxamer and poloxamine series that comprise block copolymers of polyoxyethylene and polyoxypropylene. It has been found that poloxamer 182, 183, 184, 185, 234, 282, 333, 401, 402, 403 and poloxamine 504, 904 and 1302 are particularly suitable. Any other materials which provide the desired particle surface characteristics may be used as modifying agent, including polyethylene glycol (PEG), dextran, modified dextrans such as polyethylene glycol-dextran conjugates, gangliosides, polysaccharides, phospholipids, glycolipids, proteins and mixtures and modifications thereof.

The modifying agent used desirably has a molecular weight of greater than 1000.

If the modifying agent is a polymeric material containing ethylene oxide groups, then the hydrophilic domain should preferably have less than 42 ethylene oxide groups. The polymer can be attached by adsorption, incorporation or grafting. If the materials are block copolymers of the poloxamine (Pluronic) or poloxamer (Tetronic) series, the polyoxyethylene content should prefereably be less than 80%.

The colloidal particles are preferably in the size range 1–250 nm, more preferably 1–100 nm and most preferably up to 60 nm.

The particles can be non-biodegradable, for example polystyrene particles or carbon particles, or biodegradable. The biodegradable particles suitably include microspheres and nanoparticles, microcapsules or nanocapsules, emulsions, microemulsions, liposomes and mimics of lipoproteins and chylomicrons. Suitable materials for these include polylactic acid and polyglycolic acid and their mixtures, polylactidecoglycolide mixtures, polymalic acid, polyalkylcyanoacrylates, polyanhydrides, polycaprolactones, polyphosphazenes, natural materials such as hyaluronic acid, albumin, dextran, gelatin, starch, collagen, polysaccharides and derivatives thereof and vegetable oils such as soybean oil. By derivatives we mean covalent esters and ethers of such natural materials.

The modifying agent is preferably adsorbed to the surface of the particle, but may be attached by any other method which produces a particle with the desired surface hydrophobicity may be used. For example a suitable modifying agent that is preferentially located at the particle surface may be incorporated during particle production (see FEBS 268, vol 1, 1990) 235–237 and Polymer, 1992, vol 33, No 5, 1112 onwards), suitable chemical moieties may be grated to reactive groupings on the particle surface (see Methods in Enzymology vol 112, 1985, p67 onwards), or more hydrophilic components may be phase separated during particle preparation. The term attached as used herein includes any method of incorporating the modifying agent into or grafting the modifying agent onto the particle.

An attached modifying agent can be incorporated during particle preparation and the following is an example of a suitable method.

Preparation of poly(D,L-lactide-co-glycolide and polyz (β-malic acid-co-benzyl malate) nanoparticles, sterically stabilized during production Poly(D,L-lactide-co-glycolide) or PLGA (75:25, $Mw_{GPC}$ 63 kD) was purchased in the form of Resomer® RG755 from Boehringer Ingelheim (Ingelheim, Germany). The poly (β-malic acid-co-benzyl malate)(PMLABe$_{100-x}$H$_x$, with x indicating the percentage of acidic repeating units in polymer chain, the entire range referred to by acronym, PMLABeH) copolymers of differing composition were used: PMLABe$_{100}$ (Mw 36 kD; I=1.5 according to size exclusion chromatography in dioxane calibrated using polystyrene standards), PMLABe$_{90}$H$_{10}$ and PMLABe$_{80}$H$_{20}$ (derived from the PMLABe$_{100}$ by partial hydrolysis). Poloxamer 407 and 188, and Poloxamine 908, 904 and 1504 (BASF Corporation, USA) were used as purchased.

The copolymer (PLGA, PMLABe$_{100}$, PMLABe$_{90}$H$_{10}$, or PMLABe$_{80}$H$_{20}$) was dissolved in acetone (10 ml, 20.0 mg/ml for PLGA or 5.0 mg/ml for PMLABeH) and a mixture of deionized water and ethanol (1:1) was added dropwise (25G syringe needle) into the copolymer solution stirred by magnetic stirrer (Ika-Labortechink, Germany), until turbidity indicative of copolymer precipitation was visualy observed. The suspension of these preformed nanoparticles was then added to an aqueous surfactant solution (15 ml) placed in a glass beaker (50 ml) and agitated by a magnetic stirrer at ambient temperature until complete evaporation of the organic solvent had taken place. The aqueous surfactant solution consisted—of poloxamer and poloxamine stabilizers in concentrations of 1.0% w/v. The nanoparticles were separated from the preparation media by passing through a chromatography column (C 40/26 Pharmacia, Uppsala, Sweden) packed with Sepharose 4B gel (Pharmacia, Uppsala, Sweden) using deionized water as the eluent (flow rate 1.5 ml/minute).

A suitable particle with a grafted modifying agent would be for example human serum albumin microspheres in the size region 80–140 nm with a grafted surface PEG chain. These can be prepared by precipitating a 2% solution of human serum albumin-polyethylene glycol co-polymer in a water/accetone mixture with ethyl acetate during stirring. The microspheres are crosslinked with glutaraldehyde.

Alternatively human serum albumin microspheres with surface grafted PEG chains can be produced by mixing a solution of DextranolxPEG with acetone and PEG 400, adding a 20% solution of human serum albumin dropwise to the mixture and stirring overnight. The dextranoxPEG (a copolymer of modified dextran and PEG) crosslinks the albumin by means of the active aldehyde functions on the modified dextran molecules.

Microparticles with covalently bonded PEO chains, grafted particles, can be produced by a copolymerisation process. An example is the use of a polyethylene glycol macromonomer with styrene. The composition of the copolymerisation reaction mixture can be varied to prepare microparticles with varying amounts of macromonomer in the surface.

The surfactant-free copolymerization of styrene with PEG2000 is based on the method used by Ottewill et al (Br. Polym. J 19, 435, 1987) using potassium persulphate as the initiator. The polymerization was performed in a three-necked round-bottomed flask under constant nitrogen flow with a water cooled reflux condenser and a thermometer placed in the other two outlets. The reaction flask was maintained at a constant temperature (70° C.) using a thermostatted oil bath and the flask contents were stirred by a magnetic stirrer at constant speed. Ultrapure water was added to the flask and allowed to equilibrate to 70° C. at which time styrene was added to the flask beneath the surface of the water (to minimise evaporation) through one outlet. The PEG2000 (dissolved in ultrapure water) and the initiator potassium persulphate (dissolved in ultrapure water) were added separately, immediately after the styrene and the reaction was allowed to proceed for 24 hours at 70° C.

The resulting latices were filtered through Watman No 1 filter paper (UK) and then a portion of each latex cleaned by dialysis as follows. Approximately 20 ml latex was dialysed against 900 ml ultrapure water for two weeks replacing the dialysate daily.

Suitable liposome systems can be prepared with a mixture of phospholipids and cholesterol. The molar ratio can be varied for the desired composition. Polyethyleneglycol-phosphatidylethanolamine is an example of a modified phospholipid that can be used to provide liposomes with appropriate surface characteristics.

The preparation of liposomes containing polyethyleneglycol phospholipids is well described in the literature (see for example, Litzinger and Huang. Biochim. Biophys. Acta. 1127, 249 1992).

The polyethyleneglycol phospholipid is added to a mixture of phospholipid and cholesterol in chloroform. The lipid mixture is placed in a round bottom glass tube and the organic solvent is evaporated under vacuum. The lipid film so obtained is suspended by the addition of buffer to form multilamellar liposomes. Sonication or passage of these liposomes through nucleopore filters results in the formation of small unilameller vesicles.

The composition should preferably achieve the following distribution when measured in the rat-foot pad model at 24 hours:

(i) less than 25% of the dose remaining at the injection site (ii) at least 20% of the dose located in the primary and secondary lymph nodes (iii) good distribution between the nodes with at least 5% in the primary nodes and at least 5% in the secondary nodes.

Such a lymphatic delivery composition will be advantageous for many applications to include:

(i) imaging and visualisation modalities such as lymphangiography, lymphoscintigraphy, computer assisted tomography (CAT), magnetic resonance imaging, ultrasound. These techniques provide information regarding detection of neoplastic involvement, particularly of inaccessible nodes in patients with malignant diseases. Knowledge on the size of the node and the filling of nodes can also be instructive.

The particles so directed to the lymph nodes in diagnostic applications will contain suitable contrast or imaging agents such as ferromagnetic materials such as iron oxide, perfluorochemicals such as perflurooctylbromide, or radiolabels such as technetium-99m, Indium-111, Iodine-131 or 123 or those produced by neutron activation such as samarium-153.

(ii) Radiation therapy. The use of radionuclide labelled colloids such as 198-Au and 90-Y or oils radiolabelled with 131-I for the ablation of metastatic disease.

(iii) The delivery of drugs to lymph nodes using carriers such as microspheres, microcapsules, emulsions, liposomes. Agents and diseases relevant in this regard include antimicrobial agents for treatment of infection of the nodes such as in filariasis, brucellosis, tuberculosis and HIV, antitumour agents such as mitomycin C, bleomycin, etc. or antibodies against tumours and macrophage modifying agents such as interferons, MDP, cyclosporin, etc.

The compositions may be administered by standard methods and particularly by subcutaneous injection. The compositions should satisfy the usual requirements for injection and are therefore administered in sterile, non-pyrogenic and preferably non-inflammatory solutions such as saline. Single or multiple injections can be used for administration of the compounds. The dose administered depends on the anatomical area to be treated or investigated and typically the volume of solution injected is less than about 0.5 ml.

BRIEF DESCRIPTION OF THE DRAWINGS

A preferred embodiment of the invention will now be described in more detail with reference to the accompanying drawings in which.

Figure 1:
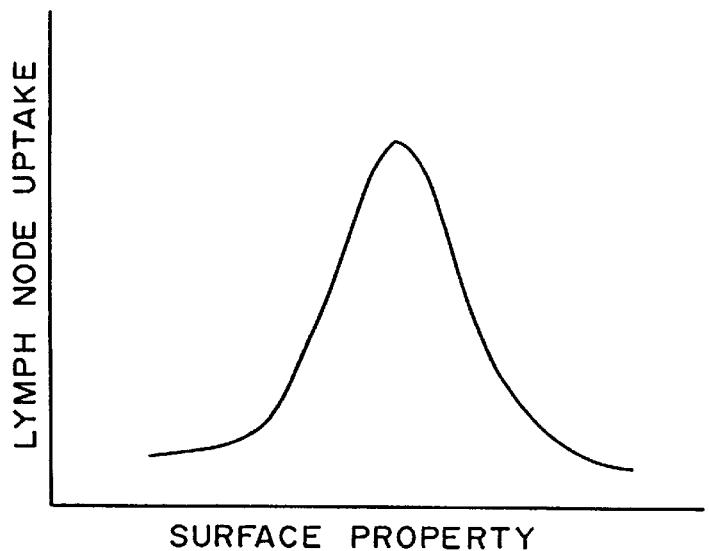
FIG. 1 is a graphical illustration of the relationship between particle surface property and lymph node uptake.

We have found that uptake of colloidal particles by lymph nodes is surprisingly increased by modifying the surface of the particles to have an intermediate hydrophobicity/hydrophilicity. In this way we have achieved an uptake of at least 15% of the administered dose in the primary and secondary lymph nodes with at least 5% in each of the primary and secondary nodes and less than 25% of the dose remaining at the injection site.

The definition of intermediate hydrophobicity/hydrophilicity required by the particles is based on concepts of surface free energy (contact angles or hydrophobic interaction chromatography or albumin uptake ratio) or thickness of the layer of the modifying agent. These concepts and the measurement of objective parameters have been discussed previously by the present inventors and others, see Muller, R. H., Davis, S. S. and Mak, E. in Advances in Separations using Aqueous Phase Systems, Applications in Cell Biology and Biotechnology, Eds. Fisher et al, Plenum Press, New York, 1989, pp 149–155. Muller, R. H., Davis, S. S., Illum, L. and Mak, E. in Targeting of Drugs with Synthetic Systems. Eds. Gregoriadis et al. Plenum, New York, 1986, pp 239–263.

Contact Angle

The contact angle between a surface and a solution of the modifying agent can be used as a measure of surface hydrophobicity. The method used is that described by Troster, S. D. and Kreuter, J. Contact angles of surfactants with a potential to alter body distribution of colloidal drug carriers on poly(methyl methacrylate) surfaces. Int. J. Pharm. 45 (1988) 91–100. The contact angle measured is the advancing contact angle between an aqueous 0.2% solution of the block copolymer and a plane surface of a reference polymeric material, in our case polystyrene. The greater the value of the contact angle, the more hydrophilic is the nature of the modifying agent. A low value of the advancing contact angle indicates lower hydrophilicity.

The following method can be used.

Glass microscopy slides were cleaned prior to use by soaking in chromic acid and then washing with copious amounts of double distilled water. In order to ease adhesion of the polystyrene film to the slides, they were pre-silanised by submersion in a solution of 0.5% dichlorodimethysilane in dichloromethane for 10 sec, rinsed with acetone then distilled water, and dried at 70° C. for 12 hr. The slides were then dipcoated with polystyrene by a single immersion into a 5% solution of polystyrene (MW 40,000; BDH, Poole, UK) in toluene and left to dry at 70° C. for 12 hr in a dust free atmosphere.

0.2% w/v solutions of the modifying agents in double distilled water were prepared using glassware pre-cleaned as described above. Advancing contact angles of a 3 µl drop on polystyrene coated slides were measured at time zero using a contact angle goniometer (Troster and Kreuter, 1988; Van Oss and Gillman, 1972). The results are presented as the mean of the contact angle measurements for ten separate drops±SD. The procedure is carried out at room temperature.

For grafted surfaces a similar procedure can be adopted where the surface groups are grated to the surface of a suitably treated glass slide and the contact angle of a drop of water measured. For the measurement of the surface hydrophobicity of polystyrene grafted with polyethyeneglycol (PEG), the PEG-polystyene co-polymer (produced as described in Polymer, 33 (5), 1992, 1112) was coated all to silanised glass slides by dipping these into a 5% solution of the co-polymer in toluene and drying by evaporation. The advancing contact angle was measured of a 3 µl drop of distilled water using a goniometer.

Hydrophobic interaction chromatography (HIC)

The hydrophobicity-hydrophilicity of a particle can be determined by HIC as discussed by Muller et al. (1989) cited above. This approach has been adapted from techniques described in the field of microbiology. In the present invention we have used the following procedure based upon the material butyl agarose. A butyl agarose column (bed volume 2.5 ml; Sigma. UK) was used. 150 µl of a 0.1% w/v 60 mm polystrene particles suspension in 0.1% w/v of polymer solution (incubated overnight) was loaded onto the column and eluted with 5 ml of phosphate buffer (pH 6.8, 0.02M) containing 0.2 M NaCl (elution peak). The column was then washed with buffer containing 0.1% v/v Triton X-100 until all the particles had been recovered (washed peak).

The procedure was carried out at room temperature.

Particle detection was by means of a flow through Cecil CE272 UV spectrophotometer at 380 nm. The method of cut and weigh was used to determine the peak areas obtained, and the HIC ratio calculated as defined below:

$$HIC\ \text{ratio} = \frac{\text{Area of elution peak}}{\text{Area of wash peak}}$$

Thickness of the layer of modifying agent

The thickness of the layer of a modifying agent which is adsorbed to the particle surface can be measured by various techniques. We have employed a method known as photon correlation spectroscopy (PCS)(laser light scattering). In this method, standard particles of, for example, polystyrene of a size similar to that to be used in animal experiments is equibrated with a concentration of polymer in aqueous solution such that at equilibrium the concentration remaining in the bulk phase will provide conditions such that adsorption is occurring in the plateau region of the adsorption isotherm. This plateau region is described in more detail in the publication of Kayes and Rawlins, Colloid Polymer Sci. 257, 622–629 (1979). The size of these particles is determined by the PCS method and is compared to that of control particles of identical properties which have not been incubated with the polymer. Half of the difference in size is the adsorbed layer thickness. Particle solutions were incubated overnight at the concentrations of 0.1% w/v particles suspensions in 0.1% w/v of polymer solution prior to measurement of the adsorbed layer thickness by Photon Correlation Spectroscopy.

Immediately prior to measurement the samples were diluted with McIlvaine buffer (pH 7;) to a low concentration, and then centrifuged at 2000 rpm for 5 minutes to remove any dust or aggregates. Measurements were then conducted using a Malvern apparatus using a correlator sample time of 20 µs. The size was taken to be the mean of 12 measurements and the absorbed layer calculated by comparison of the mean with the size of uncoated particles.

Where the modifying agent is incorporated or grafted onto the surface of the particles, the thickness of the layer of modifying agent can be determined by rheological measurements, as described by Tadros in (Polymer colloids as models for studying inferfacial forces in concentrated dispersions in F. Candau and R H Ottewill (eds), Scientific Methods for the Study of Polymer Colloids and Their Applications, Kluwer Academic Publishers, Netherlands, 1990, pp 393–411) and by Prestidge and Tadros (Viscoelastic Properties of aqueous concentrated polystyrene latex dispersions containing grafted poly (ethylene oxide) chains, J. Colloid Interf. Sci, 124, 1988, 660–665), or Costello et al, J. Colloid Interface Sci, 152, 237, 1992.

In this method the adsorbed layer or the layer of a grafted hydrophilic polymer such as PEG can be measured by studying the relation between relative viscosity and effective volume fraction of a high concentrated dispersion of particles.

A reliable semi-empirical equation for the relative viscosity of a dispersion in terms of particle volume fraction is given by $$\eta_r = [1 - \theta/\theta_p]^{-|\nu|\theta_p},$$

the Dougherty-Krieger equation while [η] is the intrinsic viscosity and is equal to 2.5 for hard spheres, $\theta_p$ is the maximum packing fraction which is taken to be equal to 0.7.

When the particles have a layer of polymer their volume fraction is increased to give an effective volume fraction $\theta_{\mathit{eff}}$ and this effective volume fraction is directly related to the thickness (δ) of the polymer layer by the equation:

$$\varnothing_{\mathit{eff}} = \varnothing\left[1 + \left(\frac{\delta}{R}\right)\right]^3$$

θ being the maximum packing fraction of the particle dispersion and R the radius of the particle.

Rheological measurements can be conducted using a Haake-Rotovisco (Model RV100) fitted with a M500/M150 head, concentric cylinder geometry. The experiments are conducted at 25° C. Flow curves showing the relation between steady shear stress and shear rate are recorded on an X-Y recorder. The values of the relative viscosity are obtained from the gradients of such curves. For low volume fractions the curves are linear throughout, demonstrating Newtonian behaviour. For systems with higher volume fraction the dispersions are non-Newtonian and the linear portion of the flow curve is used.

The value of δ is obtained by an iterative process wherein values of δ are used to fit the experimental points to the theoretical curve given by the Dougherty-Krieger equation.

This method can also be used to determine an adsorbed layer thickness as follows.

Polystyrene dispersion at 8% volume fraction of average size, 250 nm, are coated with an adsorbed layer of block copolymer by equilibration for 24 hours in a 1% w/v solution of the copolymer at 25° C.

Dispersions of such coated systems or PEG-grafted with various volume fractions are prepared and measured as above in terms of their relative viscosities. Systems of high volume fraction are prepared by centrifugation of more dilute systems. Volume fractions in the range 0.3 to 0.6 are selected.

The thickness of a grafted layer of modifying agent can also be measured by small angle neutron scattering (SANS) according to the method described in Harris et al, 'Determination of the adsorption of surface active agents by small angle scattering' in 'Adsorption from solution', Eds, Ottewill et al p139, Academic Press 1983 or p287 Cogrove et al, An experimental study of polymer conformations at the solid/solution interface.

Adsorption of human serum albumin

The relative hydrophobicity of a particle surface can also be determined by the uptake of a probe material such as a protein. It is well known that hydrophobic particles strongly adsorb proteins such as human serum albumin, while hydrophilic surfaces adsorb much less. Thus a scale of relative hydrophobicity can be created by studying the adsorption of a single purified protein species to a plane surface or to the surface of particles. The amount adsorbed in terms of milligrams per unit surface area, can be used as a suitable parameter. Preferably the albumin uptake ratio (AUR) is used and this is defined as the ratio of the amount taken up on a test surface in comparison to a control surface.

The AUR can be determined by the following method. To 20.0 ml of 0.5 mg/ml human serum albumin (HSA) solution, 246 μl of HSA-labelled with iodine-125 was added. The specific activity of the HSA solution was 8840 cpm/μg. The particles under study and any reference particles at a known concentration and particle size were incubated with the radio labelled albumin. Thus 1 ml of 2% (w/v) poloxamer or poloxamine solution were incubated overnight with 1 ml of 2% (w/v) polystyrene particles of 250 nm diameter. To 0.3 ml of the particle suspension 0.2 ml of buffer was added followed by 1.0 ml of labelled HSA added dropwise. Controls were prepared containing HSA and poloxamer or poloxamine. Incubation lasted 12 hours (the incubation tubes were precoated with 4 ml of 1 mg/ml HSA solution. After 2 hours the mixture was discarded and the tube rinsed three times with water.) After incubation, the particles were centrifuged at 13,500 rpm until pelleted. The particles were washed and sonicated to provide an even resuspension. The amount of labelled HSA attached to the particles was determined using a gamma counter.

Specific embodiments of the invention and the control experiments are now provided.

EXAMPLE 1

Polystyrene particles (Polysciences Ltd UK) of a particle size of 60 nm as determined by PCS were surface labelled with Iodine-125 using the method of Huh Y., Donaldson, G. W., and Johnston, F. J., A Radiation-induced bonding of iodine at the surface of uniform polystyrene particles. Radiation Research 60, 42–53 (1974). The labelled particles were cleaned by dialysis and then incubated with a series of block co-polymers of the poloxamer and poloxamine series. These block copolymers contain polyoxyethylene and polyoxypropylene groups. The concentration of block copolymer was 0.1%. Aliquots of unlabelled particles were also incubated in the same way and their HIC parameter and adsorbed layer thicknesses determined. The corresponding contact angle values were measured using a 0.2% aqueous solution of the polymer and a plane polystyrene surface.

Particles were injected into groups of rats (n=4). In all experiments, male Wistar rats weighing 160–200 g received 100 μl of injection volume (0.1 mg polystyrene particles iodine-125 labelled; 0.1% w/v polymer) by subcutaneous injection into the hind foot pads, under halothane anaesthetic. After blood sampling then sacrifice at 24 hours, the regional lymph nodes, namely the popliteal, iliac and renal nodes, and major body organs were removed and counted in a gamma counter for associated Iodine-125 activity. The results were calculated as a % of administered dose and expressed as the mean±sd of four injections. The results are summarised in Table 1. The results show that coating agents such as poloxamines and poloxamers can improve the rate

TABLE 1A

Uptake of coated colloidal particles by regional lymph notes in the rat foot pad model Data at 24 hours post injection.

| Coating Polymer | Injection site | Primary | Regional Lymph Nodes Secondary | Total | T/I ratio |
|---|---|---|---|---|---|
| Poloxamers | | | | | |
| 101 | 30.8 ± 6.2 | 6.97 ± 2.53 | 2.00 ± 0.81 | 8.99 ± 3.09 | 0.292 |
| 105 | 32.8 ± 1.8 | 10.68 ± 1.23 | 23.18 ± 2.04 | 12.94 ± 3.09 | 0.394 |
| 108 | 29.4 ± 1.2 | 7.44 ± 3.39 | 4.55 ± 2.25 | 12.12 ± 2.97 | 0.412 |
| 124 | 15.6 ± 6.3 | 8.27 ± 0.06 | 2.79 ± 2.18 | 11.56 ± 1.56 | 0.741 |
| 181 | 34.3 ± 6.3 | 8.79 ± 2.73 | 1.87 ± 1.43 | 10.75 ± 3.79 | 0.313 |
| 182 | 19.6 ± 1.9 | 10.55 ± 0.82 | 10.86 ± 0.52 | 21.93 ± 31.3 | 1.119 |
| 183 | 21.4 ± 0.3 | 11.97 ± 3.99 | 11.68 ± 3.6 | 24.24 ± 4.34 | 1.133 |
| 184 | 22.0 ± 2.8 | 18.45 ± 6.25 | 9.26 ± 5.74 | 28.53 ± 1.04 | 1.298 |
| 185 | 19.2 ± 1.2 | 14.49 ± 3.92 | 14.91 ± 3.34 | 29.49 ± 6.24 | 1.536 |
| 188 | 17.9 ± 6.0 | 5.02 ± 2.20 | 9.08 ± 2.25 | 14.82 ± 5.15 | 0.828 |
| 234 | 11.8 ± 1.6 | 19.46 ± 1.22 | 5.57 ± 4.33 | 25.17 ± 5.61 | 2.133 |

TABLE 1A-continued

Uptake of coated colloidal particles by regional lymph notes in the rat foot pad model Data at 24 hours post injection.

| Coating Polymer | Injection site | Regional Lymph Nodes Primary | Secondary | Total | T/I ratio |
|---|---|---|---|---|---|
| 238 | 15.6 ± 1.8 | 0.94 ± 0.24 | 0.36 ± 0.35 | 1.46 ± 0.32 | 0.094 |
| 282 | 12.8 ± 0.3 | 7.23 ± 5.62 | 13.55 ± 2.30 | 21.79 ± 4.51 | 1.702 |
| 288 | 11.8 ± 1.0 | 0.44 ± 0.35 | 0.22 ± 0.18 | 0.79 ± 0.41 | 0.067 |
| 333 | 11.8 ± 2.3 | 12.44 ± 4.78 | 6.39 ± 1.43 | 21.48 ± 7.32 | 1.820 |
| 338 | 9.6 ± 1.8 | 0.59 ± 0.24 | 0.26 ± 0.01 | 0.99 ± 0.13 | 0.199 |
| 401 | 15.5 ± 1.1 | 7.10 ± 1.18 | 16.73 ± 1.89 | 28.62 ± 3.64 | 1.843 |
| 402 | 11.6 ± 3.3 | 6.08 ± 1.06 | 10.70 ± 1.74 | 20.96 ± 2.44 | 1.807 |
| 403 | 12.3 ± 0.8 | 2.72 ± 1.17 | 5.90 ± 2.55 | 13.59 ± 4.09 | 1.105 |
| 407 | 11.1 ± 1.4 | 0.52 ± 0.21 | 0.51 ± 0.24 | 1.07 ± 0.39 | 0.096 |
| Poloxamines | | | | | |
| 304 | 29.4 ± 0.6 | 5.25 ± 4.89 | 1.82 ± 1.35 | 7.09 ± 4.97 | 0.241 |
| 504 | 18.5 ± 3.5 | 13.95 ± 2.33 | 11.05 ± 1.12 | 25.00 ± 2.00 | 1.351 |
| 704 | 14.9 ± 4.8 | 5.93 ± 1.18 | 15.70 ± 1.85 | 27.47 ± 2.47 | 1.846 |
| 901 | 45.0 ± 9.4 | 1.94 ± 0.20 | 0.41 ± 0.33 | 2.36 ± 0.19 | 0.052 |
| 904 | 13.0 ± 3.1 | 2.97 ± 0.82 | 10.73 ± 2.08 | 18.04 ± 2.70 | 1.388 |
| 908 | 22.1 ± 3.2 | 0.68 ± 0.16 | 0.53 ± 0.15 | 1.23 ± 0.27 | 0.056 |
| 1104 | 14.8 ± 4.1 | 2.75 ± 1.58 | 8.02 ± 4.49 | 11.63 ± 4.96 | 0.786 |
| 1302 | 19.1 ± 6.2 | 14.60 ± 0.39 | 4.94 ± 1.07 | 19.55 ± 0.68 | 1.024 |
| 1304 | 10.6 ± 1.1 | 1.34 ± 0.17 | 1.83 ± 0.26 | 3.28 ± 0.51 | 0.309 |
| 1504 | 12.9 ± 0.5 | 0.79 ± 0.31 | 0.93 ± 0.19 | 1.79 ± 0.28 | 0.139 |
| 1508 | 15.9 ± 2.3 | 0.54 ± 0.17 | 0.37 ± 0.12 | 1.00 ± 0.34 | 0.063 |

TABLE 1B

Physicochemical data for coated particles

| Coating Polymer | Adsorbed layer thickness (nm) | HIC Ratio | Contact angle (°) |
|---|---|---|---|
| 101 | 0.15 | 0.06 ± 0.03 | — |
| 105 | 0.19 | 0.56 ± 0.09 | — |
| 108 | 0.99 | 0.78 ± 0.11 | — |
| 124 | 0.04 | 1.23 ± 0.18 | — |
| 181 | 0.19 | 0.13 ± 0.05 | 43.7 ± 0.9 |
| 182 | 0.79 | 1.71 ± 0.32 | 47.1 ± 0.9 |
| 183 | 0.76 | 1.95 ± 0.16 | 47.8 ± 1.1 |
| 184 | 1.01 | 2.13 ± 0.06 | 49.0 ± 0.7 |
| 185 | 1.64 | 3.25 ± 0.13 | 53.5 ± 1.0 |
| 188 | 4.19 | 5.39 ± 0.43 | 63.2 ± 1.2 |
| 234 | 1.55 | 3.65 ± 0.29 | — |
| 238 | 8.45 | 17.39 ± 0.77 | — |
| 282 | 1.26 | 2.09 ± 0.11 | — |
| 288 | 7.34 | 19.76 ± 0.24 | — |
| 333 | 2.76 | 4.14 ± 0.52 | — |
| 338 | 7.47 | 20.31 ± 0.76 | — |
| 401 | 1.24 | 4.02 ± 0.25 | 32.1 ± 1.9 |
| 402 | 2.36 | 3.87 ± 0.06 | 24.1 ± 1.7 |
| 403 | 3.09 | 4.54 ± 0.11 | 27.3 ± 1.6 |
| 407 | 6.05 | 18.37 ± 4.57 | 56.2 ± 1.0 |
| Poloxamines | | | |
| 304 | — | 0.21 ± 0.04 | — |
| 504 | 0.84 | 1.66 ± 0.25 | — |
| 704 | 1.34 | 4.21 ± 0.61 | — |
| 901 | 0.43 | 0.62 ± 0.19 | 27.6 ± 1.2 |
| 904 | 1.67 | 3.35 ± 0.68 | 44.3 ± 1.2 |
| 908 | 8.14 | 18.65 ± 1.58 | 69.0 ± 1.1 |
| 1104 | 2.57 | 5.17 ± 0.446 | — |
| 1302 | 3.00 | 3.67 ± 0.67 | — |
| 1304 | 3.79 | 5.33 ± 0.25 | — |
| 1504 | 4.89 | 5.68 ± 0.61 | — |
| 1508 | 9.39 | 15.50 ± 2.31 | — | of drainage of small particles from a subcutaneous injection site. Certain materials increases the sequestration of polystyrene microspheres in the lymph nodes by a surprising amount in comparison to uncoated particles and those coating agents previsouly described in the prior art. The uptake is more pronouced in local (primary) than distal modes (secondary and tertiary). These results demonstrate that the highest lymph node uptake an be achieved by the appropriate selection of a particle with a modified surface. The uptake is far greater than has been obtained previously for any reported colloidal system. It is useful to calculate a ratio in terms of the amount in the lymph nodes relative to that at the injection site. This value demonstrates the degree to which the particles move from their administration site to the target site.

For effective targeting we define that at least 20% of the dose should reach the target site(s) at 24 hours and that the ratio of lymph node uptake to injection site should be greater than 1.0 as measured in the rat model as described above. Furthermore, good distribution, i.e. between the primary and secondary lymph nodes is desirable with at least 5% appearing in the primary nodes and 5% in the secondary nodes. It can be seen from the results in Table 1 that such distribution is only achieved by using those materials which give an intermediate hydrophicity/hydrophilicity to the particle surface.

Figure 2:
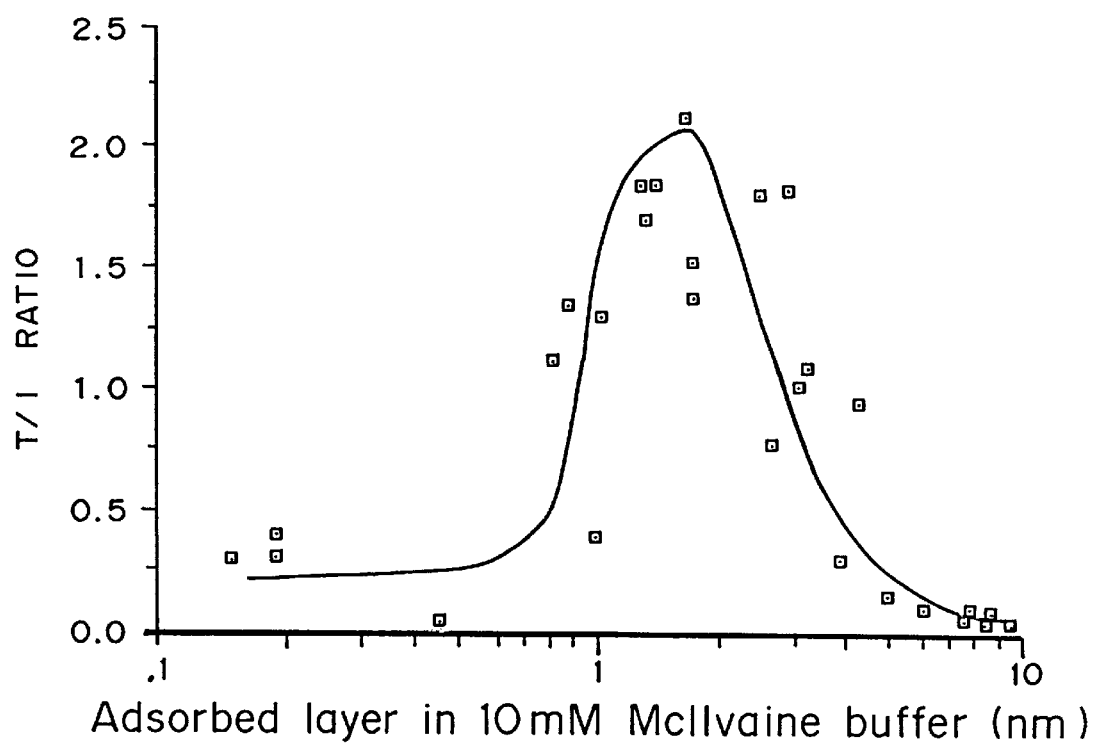
FIG. 2 illustrates the relationship between the adsorbed layer thickness and the lymph node uptake expressed as the ratio of amount of particles at the injection site to that in the nodes.
Figure 3:
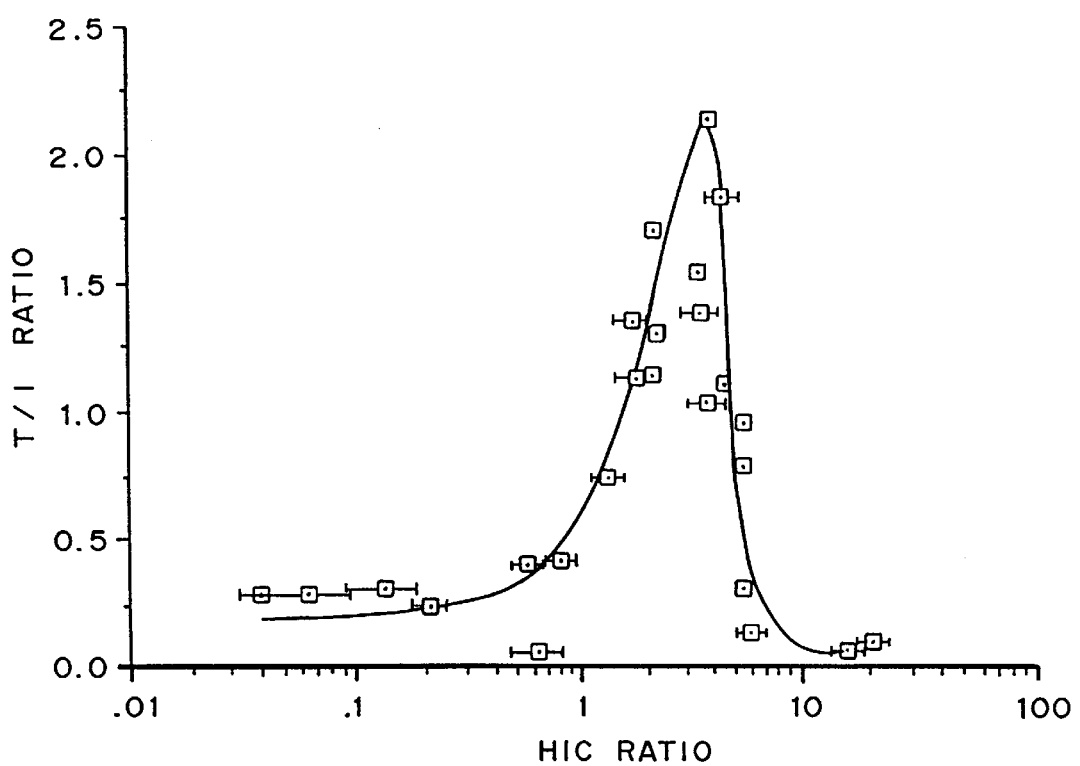
FIG. 3 illustrates the relationship between the hydrophobicity ratio and the lymph node uptake expressed as in FIG. 2.
Figure 4A:
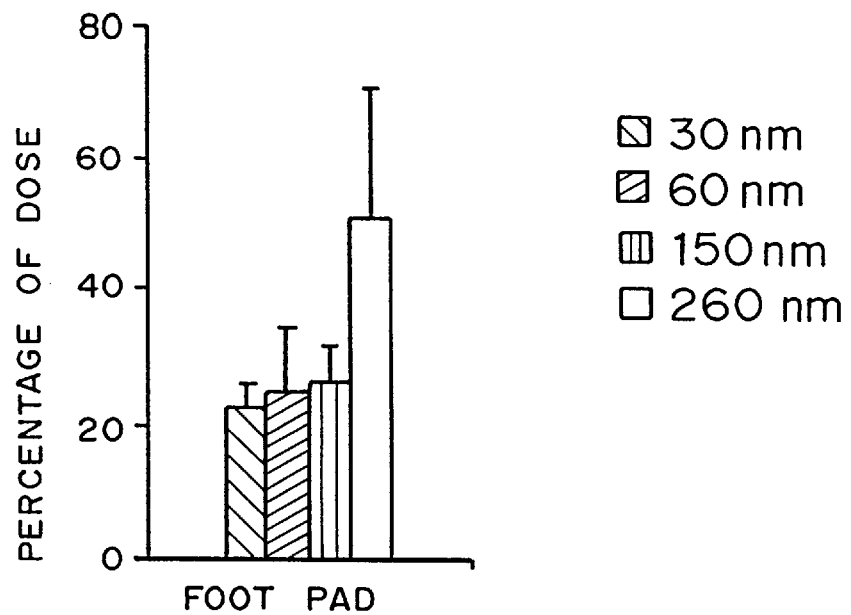
FIG. 4a illustrates the effect of particle size on particle retention after 24 hours at the injection site.
Figure 4B:
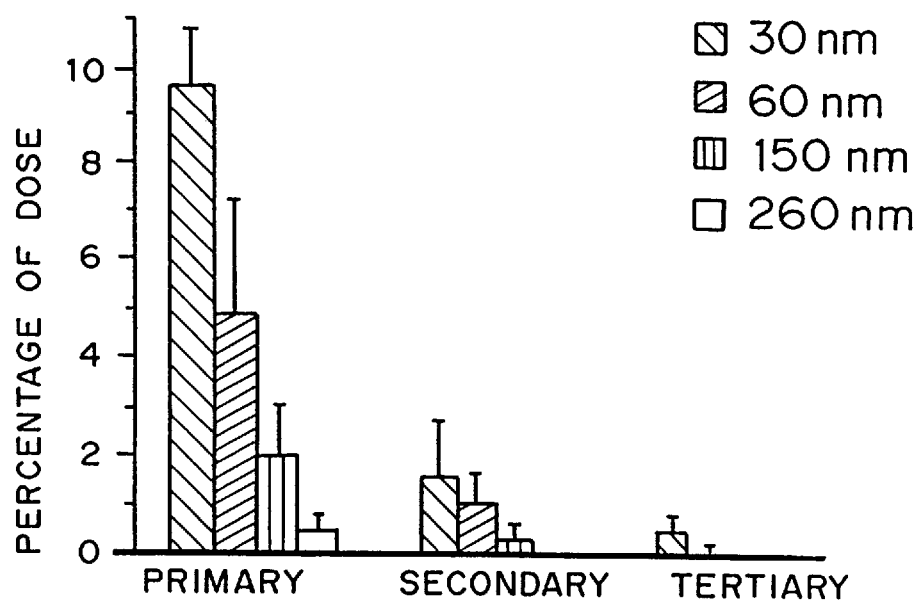
FIG. 4b illustrates the effect of particle size on particle retention after 24 hours at the regional lymph nodes.

The relationship between the adsorbed layer thickness of the materials tested and the lymphatic uptake of particles, expressed as the ratio of the amount of particles in the lymph nodes to that at the injection site, is shown in FIG. 2. From this it can be seen that the uptake is greatest for particles with an adsorbed layer thickness of between 0.8 and 4.0 nm.

The relationship between the HIC ratio of the materials tested and the lymphatic uptake of particles, expressed as the ratio of the amount of particles in the lymph nodes to that at the injection site, is shown in FIG. 3. From this it can clearly be seen that the uptake of particles by the lymph nodes is greatest for particles with an intermediate hydrophobicity/hydrophilicity, particularly for particles with an HIC ratio of between 0.5 and 10 and is greatest for particles with a HIC ratio of about 4.

EXAMPLE 2 (COMPARATIVE EXAMPLE)

The same 60 nm polystyrene particles were also coated with the Cremophor materials, EL RH40 and RH60 (polyethylated castor oil, polyoxyethylene 40 and 60, hydrogenated castor oil) and Tergitol materials, NP10, NP40, 15-S-9, 15-S-15 (nonoxynol 10, 40, Pareth 9 and 15) described in the patent GB 2108967 (Table 2). Concentrations of 0.1% were employed for the coating step. Uncoated particles and particles coated with poloxamine-904 were used as controls. For all these materials except poloxamine 904 the performance was poor. The uptake of the coated particles in the lymph node was low and high quantities were retained at the site of administration.

EXAMPLE 3

In the majority of the experiments the particles were injected together with the carrier polymer solution. To confirm that it is the adsorbed layer of polymer that is critical in determining lymph node uptake rather than an effect of the polymer acting as a surfactant and thereby modifying the particle penetration properties of the tissues, a series of experiments was conducted wherein the unadsorbed polymer was removed from the solution by dialysis against one liter of water in 50,000 MW cut-off tubing (Spectrum, UK). The dialysate was sampled and changed daily until the iodine assay of Baleux (Baleux, M. B., C. R. Acad. Sci. Paris 274 1617 (1972)) indicated that excess polymer was no longer present. The coating polymers chosen were Poloxamine

TABLE 2

Lymphatic Uptake of 60 nm Polystyrene Particles Coated with Tergitols and Cremophors

| Organ | Control | Poloxamine 904 | Cremophor RH40 | Cremophor RH60 | Cremophor EL |
|---|---|---|---|---|---|
| Injection Site | 44.4 ± 4.1 | 23.6 ± 4.0 | 41.7 ± 7.0 | 36.2 ± 4.6 | 27.1 ± 1.9 |
| 1° nodes | 3.41 ± 0.29 | 11.02 ± 4.65 | 5.45 ± 2.40 | 4.59 ± 1.29 | 6.80 ± 2.68 |
| 2° node | 0.56 ± 0.34 | 8.97 ± 1.07 | 1.08 ± 0.65 | 2.54 ± 2.18 | 0.86 ± 0.60 |
| 3° node | 0.01 ± 0.00 | 0.04 ± 0.06 | 0.04 ± 0.03 | 0.14 ± 0.19 | 0.03 ± 0.04 |
| Total in Nodes | 3.97 ± 0.63 | 17.43 ± 2.04 | 6.57 ± 2.23 | 7.27 ± 1.22 | 7.69 ± 2.64 |

| Organ | Tergitol NP10 | Tergitol NP40 | Tergitol 15-S-9 | Tergitol 15-S-15 |
|---|---|---|---|---|
| Injection Site | 41.0 ± 3.6 | 36.0 ± 3.1 | 38.1 ± 2.4 | 48.1 ± 10.8 |
| 1° nodes | 5.47 ± 1.49 | 8.09 ± 1.92 | 5.58 ± 0.82 | 4.68 ± 2.76 |
| 2° node | 1.41 ± 0.28 | 1.65 ± 0.75 | 0.63 ± 0.48 | 0.32 ± 0.36 |
| 3° node | 0.04 ± 0.03 | 1.14 ± 2.27 | 0.01 ± 0.01 | 0.01 ± 0.00 |
| Total in nodes | 6.92 ± 1.62 | 10.48 ± 3.22 | 6.23 ± 1.04 | 5.00 ± 2.79 |

904 and Poloxamine 908. The results are shown in Table 3. The results demonstrate that the targeting effects found with certain of the poloxamers and poloxamines is due to the presence of the modified surface layer rather than to the polymer acting as some form of penetration enhancer. Indeed removal of the excess coating polymer can increase further the lymphatic uptake of the coated particles for the case of Poloxamine 904.

EXAMPLE 4 (COMPARATIVE EXAMPLE)

In order to demonstate the superior performance of the present invention in comparison to an existing lymph targeting system, studies were performed as described in example 1 wherein the particles were Solco Nanocoll, (Solco AG Basle Switzerland). This is a colloidal suspension made from albumn particles labelled with technetium-99m. It is stated that typically 95% of the labelled colloid is below 80 nm in size as assessed by microfiltration. The results shown in table 4 demonstrate that this commercial lymph imaging agent, provides less than 10% of the administered dose to the lymph nodes at 24 hours. Tho ratio of total lymph node uptake to injection site is less than 0.5.

EXAMPLE 5

In order to follow the time course of particle uptake the experiments as described in example 1 were repeated with uncoated particles (control) and particles coated with poloxamine 904 and 908.

Measurements of total lymph node up to 2 hours, 6 hours and 24 hours were made. The results in Table 5 demonstrate that the uptake into the nodes increased with time. For the preferred system using the polymeric material poloxamine 904 the uptake in the nodes at 2 hours was 21% as compared to 24% at 24 hours.

TABLE 3

Lymphatic uptake of 60 nm polystyrene particles coated with poloxamines and the effect of removal of the excess coating agent

| | Poloxamine 904 | | Ploxamine 908 | |
|---|---|---|---|---|
| | Excess | Clean | Clean | Excess |
| Injection Site | 26.6 ± 2.2 | 20.4 ± 1.8 | 18.6 ± 2.7 | 17.3 ± 1.4 |
| Primary | 21.78 ± 8.00 | 6.46 ± 2.68 | 0.695 ± 0.110 | 0.703 ± 0.039 |

TABLE 3-continued

Lymphatic uptake of 60 nm polystyrene particles coated with poloxamines and the effect of removal of the excess coating agent

| | Poloxamine 904 | | Ploxamine 908 | |
|---|---|---|---|---|
| | Excess | Clean | Clean | Excess |
| Secondary | 15.41 ± 8.81 | 10.61 ± 1.57 | 0.505 ± 0.054 | 0.436 ± 0.077 |
| Tertiary | 4.88 ± 4.00 | 4.41 ± 1.11 | 0.057 ± 0.035 | 0.126 ± 0.023 |
| Total Nodal Uptake | 39.62 ± 5.42 | 20.37 ± 3.18 | 1.238 ± 0.123 | 1.264 ± 0.096 |

TABLE 4

Uptake of Solconancoll into the Lymphatics

| Organ | 2 hours | 6 hours | 24 hours |
|---|---|---|---|
| Injection Site | 39.6 ± 5.1 | 36.8 ± 3.7 | 23.2 ± 1.2 |
| Primary nodes | 4.59 ± 1.05 | 4.57 ± 1.67 | 5.12 ± 1.12 |
| Secondary node | 3.59 ± 1.73 | 4.62 ± 0.76 | 3.54 ± 0.37 |
| Tertiary node | 0.66 ± 0.51 | 1.02 ± 0.52 | 1.22 ± 0.28 |
| Total in nodes | 8.85 ± 2.70 | 9.95 ± 1.97 | 9.55 ± 0.54 |
| Liver | 7.40 ± 1.65 | 7.89 ± 0.59 | 4.47 ± 0.46 |
| Spleen | 0.40 ± 0.02 | 0.29 ± 0.05 | 0.22 ± 0.04 |
| Kidneys | 6.00 ± 0.83 | 8.53 ± 0.27 | 8.98 ± 0.30 |
| Blood | 0.66 ± 0.18 | 0.32 ± 0.02 | 0.20 ± 0.04 |

TABLE 5

Time Course of Particle Uptake by the Lymphatics

| | 2 hours | 6 hours | 24 hours |
|---|---|---|---|
| CONTROL | | | |
| Injection Site | 52.2 ± 5.7 | 45.8 ± 2.11 | 38.1 ± 3.1 |
| Primary | 4.05 ± 0.51 | 4.99 ± 1.10 | 8.17 ± 2.98 |
| Secondary | 0.654 ± 0.058 | | 1.14 ± 0.463 |
| Tertiary | 0.071 ± 0.033 | 1.10 ± 1.85 | 0.078 ± 0.083 |
| Total in nodes | 4.77 ± 0.47 | 6.91 ± 2.04 | 9.39 ± 3.36 |
| Poloxamine 904 | | | |
| Injection site | 27.1 ± 5.4 | 24.6 ± 2.7 | 19.0 ± 2.0 |
| Primary | 7.21 ± 2.56 | 5.20 ± 0.814 | 7.08 ± 1.59 |
| Secondary | 9.11 ± 4.38 | 9.90 ± 2.71 | 12.16 ± 3.82 |
| Tertiary | 5.95 ± 2.62 | 7.48 ± 3.86 | 4.99 ± 2.80 |
| Total in nodes | 20.78 ± 4.19 | 22.83 ± 1.80 | 24.22 ± 3.01 |

TABLE 5-continued

Time Course of Particle Uptake by the Lymphatics

|  | 2 hours | 6 hours | 24 hours |
|---|---|---|---|
| Poloxamine 908 | | | |
| Injection Site | 31.8 ± 5.7 | 26.6 ± 4.1 | 17.5 ± 1.3 |
| Primary | 0.684 ± 0.293 | 1.262 ± 0.251 | 0.969 ± 0.105 |
| Secondary | 0.394 ± 0.053 | 0.372 ± 0.315 | 0.271 ± 0.028 |
| Tertiary | 0.188 ± 0.050 | 0.095 ± 0.078 | 0.032 ± 0.002 |
| Total in nodes | 1.167 ± 0.131 | 1.73 ± 0.514 | 1.27 ± 0.123 |

EXAMPLE 6

Determination of albumin uptake ratio

Method 0.55 ml of a 2% (w/v) suspension of polystyrene (PS) particles (size 248 nm) (11 mg) was incubated with 0.55 ml of 2% (w/v) solution of Poloxamer/Poloxamine in 0.005 M McIlvanes Buffer, pH 7.4. For the control 0.55 ml of buffer was added to the particles. Incubation was overnight (approx. 18 hours) at room temperature.

1 ml of above, ie 1% (w/v) suspension of coated and control PS particles (10 mg) was put into an ultracentrifuge tube, 2.5 ml of buffer was added to produce a sufficient volume to centrifuge. The particles were centrifuged in a L8-60M Ultracentrifuge from Beckman Instruments (Palo Alto, Calif.) using a 50.3 Ti rotor at 35,000 g (rmax, k factor=308) for 15 minutes, with the deceleration set at 6. The supernatant was removed and the pellet redispersed by vortexing in 3.5 ml of buffer. The particles were washed a further four times. For the middle two runs the time of centrifuging was reduced to 12 minutes. After the final wash 0.8 ml of buffer was added and the pellet was redispersed by vortexing and sonicating. The concentration of each particle system was determined by weighing in a tared ultracentrifuge tube.

All test tubes and Eppendorfs used in the study were precoated with HSA (Albutein, Alpha, Thetford UK). This was achieved by incubating the respective tubes with HSA solution 1 mg/ml at room temperature for 2 hours. After treatment the tubes were rinsed three times with distilled water.

To 65 ml of 0.5 mg/ml HSA solution, 710 µl of HSA-I$^{125}$ was added (I$^{125}$ labelled HSA (HSA-I$^{125}$), specific activity 46 kBg/µg. Prepared from HSA (Albutein) and I$^{125}$ from Amersham, Buckinghamshire). The specific activity of the labelled HSA, determined by measuring the radioactivity of five 50 µl samples, was found to be 130.10 Bq/µg.

Triplicate samples were prepared. A known volume of particles (0.168ml–0.423 ml), sufficient to yield approximately 3 mg of particles was added to a plastic 5 ml test tube. Buffer was added to 0.5 ml. 1 ml of labelled HSA was added dropwise whilst shaking at a speed of 200 on an IKA-Vibrax-VX horizontal shaker from IKA-Labortechnik (Staufen, Germany). After addition the speed of shaking was increased to 400. Incubation lasted 2 hours at room temperature.

1.2 ml (approximately 2.4 mg of particles) from each tube above was removed and put into an Eppendorf. These were centrifuged at 11,600 g for 25 minutes in an MSE Microcentaur from Fisons (England). The supernatant was removed and the particles washed three times with 1 ml of distilled water. After the final wash the pellet was not redispersed. The radioactivity of each Eppendorf was measured in a 1282 Compugamma CS, a gamma counter from LKB Wallac (Finland). The amount of HSA bound to the wall of the Eppendorf (control—no particles) was subtracted from results for the particle systems.

Results

The results are shown in Table 6. It can be seen from these results that the greatest lymph node uptake is achieved by those particles whose surfaces have an albumin uptake ratio of between 0.2 and 0.5.

TABLE 6

Relation between lymph node uptake (T/I) and adsorption of albumin to particle surface (AUR).

| Coating | Albumin uptake ratio | Lymph node uptake (T/I) |
|---|---|---|
| Control | 1.0 | 0.07 |
| 904 | 0.21 | 1.39 |
| 908 | 0.05 | 0.06 |
| 182 | 0.336 | 1.12 |
| 183 | 0.343 | 1.13 |
| 184 | 0.338 | 1.30 |
| 185 | 0.340 | 1.54 |
| 188 | 0.184 | 0.83 |
| 333 | 0.249 | 1.82 |
| 234 | 0.277 | 2.13 |
| 238 | 0.113 | 0.09 |
| 282 | 0.277 | 1.70 |
| 407 | 0.09 | 0.10 |

We claim:

1. A method for delivering an active agent to the lymphatic system of an animal, the method comprising administering to the animal a composition comprising a plurality of colloidal particles having an active agent associated with each particle, wherein the particles consist of particles having a size of between one and 250 nm and the surface of each particle has a hydrophobicity ratio determined by hydrophobic interaction chromatography of less than or equal to about 10, thereby to target the active agent to the lymphatic system of the animal.

2. The method of claim 1 wherein the hydrophobicity ratio is less than 5.

3. The method of claim 1 wherein the surface of each particle is modified by adsorption or attachment of a modifying agent.

4. The method of claim 3 wherein the modifying agent is a block copolymer comprising polyethyleneglycol.

5. The method of claim 1 wherein the composition is administered by subcutaneous injection.

6. The method of claim 5 wherein greater than 20% of the active agent is targeted to the regional lymph nodes of an animal after subcutaneous injection of the composition in the animal.

7. The method of claim 5 wherein the active agent is delivered to the primary and secondary lymph nodes of the animal after subcutaneous injection of the composition in the animal.

8. A method for delivering an active agent to the lymphatic system of an animal, the method comprising administering to the animal a composition comprising a plurality of colloidal particles and an active agent associated with each particle, wherein a modifying agent is adsorbed onto or attached to the surface of each particle, and gives an advancing contact angle is less than about 60°, thereby to target the active agent to the lymphatic system of the animal.

9. The method of claim 8 wherein the modifying agent is adsorbed onto or attached to the surface of each particle such that the thickness of the layer of modifying agent is less than about 10 nm.

10. The method of claim 8 wherein the modifying agent is a block copolymer comprising polyethyleneglycol.

11. The method of claim 8 wherein the composition is administered by subcutaneous injection.

12. The method of claim 11 wherein greater than 20% of the active agent is targeted to the regional lymph nodes of an animal after subcutaneous injection of the composition in the animal.

13. The method of claim 11 wherein the active agent is delivered to the primary and secondary lymph nodes of the animal after subcutaneous injection of the composition in the animal.

14. A method for delivering an active agent to the lymphatic system of an animal, the method comprising administering to the animal a composition comprising a plurality of colloidal particles and an active agent associated with each particle wherein a modifying agent is adsorbed onto or attached to the surface of each particle such that the albumin uptake ratio (AUR) of the surface is between about 0.2 and 0.5, thereby to target the active agent to the lymphatic system of the animal.

15. The method of claim 14 wherein the modifying agent is adsorbed onto or attached to the surface of each particle such that the thickness of the layer of modifying agent is less than about 10 nm.

16. The method of claim 14 wherein the modifying agent is a block copolymer comprising polyethyleneglycol.

17. The method of claim 14 wherein the composition is administered by subcutaneous injection.

* * * * *